US008680057B2

(12) United States Patent
Jay

(10) Patent No.: US 8,680,057 B2
(45) Date of Patent: *Mar. 25, 2014

(54) TRIBONECTINS

(75) Inventor: Gregory D. Jay, Norfolk, MA (US)

(73) Assignee: Rhode Island Hospital, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,831

(22) Filed: May 14, 2012

(65) Prior Publication Data

US 2013/0072435 A1    Mar. 21, 2013

Related U.S. Application Data

(60) Continuation of application No. 12/703,036, filed on Feb. 9, 2010, now abandoned, which is a division of application No. 12/608,462, filed on Oct. 29, 2009, now Pat. No. 8,026,346, which is a division of application No. 10/858,595, filed on Jun. 1, 2004, now Pat. No. 7,618,941, which is a continuation of application No. 09/298,970, filed on Apr. 23, 1999, now Pat. No. 6,743,774.

(51) Int. Cl.
*A61K 38/14* (2006.01)
*A61K 38/00* (2006.01)

(52) U.S. Cl.
USPC .......... 514/20.9; 514/16.7; 514/19.1; 424/9.1

(58) Field of Classification Search
USPC .............. 514/21.2, 20.9, 16.7, 19.1; 530/350, 530/300; 424/9.1
See application file for complete search history.

(56) References Cited

U.S. PATENT DOCUMENTS

| | | | |
|---|---|---|---|
| 2,487,377 A | 11/1949 | Roehner et al. | |
| 2,734,862 A | 2/1956 | Morway et al. | |
| 2,878,184 A | 3/1959 | March et al. | |
| 4,108,849 A | 8/1978 | Thomas | |
| 4,438,100 A | 3/1984 | Balslev et al. | |
| 5,260,417 A | 11/1993 | Grant et al. | |
| 5,326,558 A | 7/1994 | Turner et al. | |
| 5,403,592 A | 4/1995 | Hills | |
| 5,510,121 A | 4/1996 | Rhee et al. | |
| 5,510,122 A | 4/1996 | Sreebny et al. | |
| 5,515,590 A | 5/1996 | Pienkowski | |
| 5,605,938 A | 2/1997 | Roufa et al. | |
| 5,612,028 A | 3/1997 | Sackler et al. | |
| 5,639,734 A | 6/1997 | Esko et al. | |
| 5,639,796 A | 6/1997 | Lee | |
| 5,702,456 A | 12/1997 | Pienkowski | |
| 5,709,020 A | 1/1998 | Pienkowski et al. | |
| 5,973,224 A | 10/1999 | Fuchs et al. | |
| 6,096,728 A | 8/2000 | Collins et al. | |
| 6,291,533 B1 | 9/2001 | Fleischner | |
| 6,433,142 B1 | 8/2002 | Turner et al. | |
| 6,720,156 B2 | 4/2004 | Hutchins et al. | |
| 6,743,774 B1 | 6/2004 | Jay | |
| 6,960,562 B2 | 11/2005 | Jay | |
| 7,001,881 B1 | 2/2006 | Jay | |
| 7,618,941 B2 | 11/2009 | Jay | |
| 8,026,346 B2 | 9/2011 | Jay | |
| 2002/0009761 A1 | 1/2002 | Hutchins et al. | |
| 2002/0086824 A1 | 7/2002 | Warman et al. | |
| 2003/0069272 A1 | 4/2003 | Yerxa et al. | |
| 2003/0180948 A1 | 9/2003 | Hutchins et al. | |
| 2003/0224386 A1 | 12/2003 | Guild et al. | |
| 2004/0048325 A1 | 3/2004 | DeFrees | |
| 2004/0072741 A1 | 4/2004 | Jay | |
| 2004/0229804 A1 | 11/2004 | Jay | |
| 2007/0111327 A1 | 5/2007 | Jay | |
| 2007/0249557 A1 | 10/2007 | Jay | |
| 2010/0048458 A1 | 2/2010 | Jay | |
| 2010/0204087 A1 | 8/2010 | Jay | |

FOREIGN PATENT DOCUMENTS

| | | |
|---|---|---|
| JP | 04278061 | 10/1992 |
| WO | WO 92/13075 | 8/1992 |
| WO | WO 98/18491 | 5/1998 |
| WO | WO 00/64930 | 11/2000 |
| WO | WO 03/000056 | 1/2003 |
| WO | WO 2005/016130 | 2/2005 |
| WO | WO 2005/084684 | 9/2005 |

OTHER PUBLICATIONS

Higaki et al. (1995) "Role of Constituents in Synovial Fluid and Surface Layer of Articular Cartilage in Joint Lubrication (Part 2). The Boundary Lubricating Ability of Proteins," Journal of Japanese Society of Tribologists 40:598-604.

International Preliminary Examination Report for International Application No. PCT/US2000/010953, mailed on Jul. 19, 2001 (9 pages).

International Search Report for International Application No. PCT/US2000/010953, mailed on Nov. 24, 2000 (3 pages).

XP-002152061. Accession No. Q92954 (2 pages), created Feb. 1, 1997. "Megakaryocyte stimulating factor," from Merberg et al., In *Biology of vitronectins and their receptors*, edited by Preissner et al., 45-53. Amsterdam: Elsevier Science Publishers B.V., 1993.

(Continued)

*Primary Examiner* — Chih-Min Kam

(74) *Attorney, Agent, or Firm* — Thomas E. Jurgensen

(57) ABSTRACT

The invention features a tribonectin and a method of tribo-supplementation carried out by administering tribonectins directly to an injured or arthritic joint.

20 Claims, No Drawings

(56) References Cited

OTHER PUBLICATIONS

XP-002152062. Accession No. U70136 (6 pages), created Oct. 1, 1996. "Human megakaryocyte stimulating factor mRNA, complete cds," from Merberg et al., "A Comparison of Vitronectin and Megakaryocyte Stimulating Factor." In *Biology of Vitronectins and Their Receptors*, edited by Preissner et al., 45-53. Amsterdam: Elsevier Science Publishers B.V., 1993.

XP-000961339. Merberg et al., "A Comparison of Vitronectin and Megakaryocyte Stimulating Factor." In *Biology of Vitronectins and their Receptors*, edited by Preissner et al., 45-53. Amsterdam: Elsevier Science Publishers B.V., 1993.

Adams et al., "The Role of Viscosupplementation with Hylan G-F 20 (Synviso©) in the Treatment of Osteoarthritis of the Knee: a Canadian Multicenter Trial Comparing Hylan G-F 20 Alone, Hylan G-F 20 with Non-steroidal Anti-inflammatory Drugs (NSAIDs) and NSAIDs Alone," *Osteoarthritis and Cartilage* 3:213-225, 1995.

Jay et al., "Boundary Lubrication by Lubricin is Mediated by O-Linked β(1-3)Gal-GalNAc Oligosaccharides," *Glycoconjugate Journal* 18:807-815, 2001.

Hascall et al. "Hyaluronan: Structure and Physical Properties," in http://www.glycoforum.gr.jp/science/hyaluronan/HA01/HA01E.html, 1997.

Marshall et al., "Amelioration of Disease Severity by Intraarticular Hylan Therapy in Bilateral Canine Osteoarthritis," *Journal of Orthopaedic Research* 18:416-425, 2000.

Sabaratnam et al., "Size Selectivity of Hyaluronan Molecular Sieving by Extracellular Matrix in Rabbit Synovial Joints," *Journal of Physiology* 567:569-581, 2005.

Sarkar et al., "Disaccharide Uptake and Priming in Animal Cells: Inhibition of Sialyl Lewis$^x$ by Acetylated Gal Beta 1-->4GlcNAc Beta-O-Naphthalenemethanol," *Proc. Natl. Acad. Sci. USA* 92:3323-3327, 1995.

Notice of Opposition to a European Patent for European Application 00926303.9 filed on Dec. 11, 2009.

Communication of a Notice of Opposition for European Application 00926303.9 mailed on Dec. 22, 2009.

Communication of Further Notices of Opposition Pursuant to Rule 79(2) EPC for European Application 00926303.9 mailed on Jan. 15, 2010.

Communication of Notices ot Opposition (R. 79(1) EPC) for European Application 00926303.9 mailed on Jan. 15, 2010.

Reply to Notice of Opposition for European Application 00926303.9 filed on Nov. 19, 2010.

Aydelotte et al., *Heterogeneity of Articular Chondrocytes* (Articular Cartilage and Osteoarthritis, New York: Raven Press Ltd., 1992), 237-249.

Arnann et al., "New Potent Sialyltransferase Inhibitors—Synthesis of Donor and of Transition-State Analogues of Sialyi Donor CMP-Neu5Ac," *Chem-Eur J.* 4: 1106-1115, 1998.

Brown et al., "Glycoside Decoys of Glycosylation," *Trends Glycosci. Glyc.* 13: 335-343, 2001.

Caron, "Understanding the Pathogenesis of Equine Osteoarihritis," *Br. Vet. J.* 148(5):369-371, 1992.

Chen et al., "Influence of Trypsin on the Biological Bonding of Cartilaginous Surface to Bone in Rabbits," *Arch. Orthop. Trauma. Surg.* 120: 587-591, 2000.

Clark et al., "MSF precursor," Feb. 2, 1993, Database A_Geneseq_1101, Accession No. AAR26049.

Elsaid et al., "Association of Articular Cartilage Degradation and Loss of Synovial Fluid Boundary-Lubricating Ability Following Injury and Infiaminatory Arthritis," *Arthritis Rheum.* 52: 1746-1755, 2005.

Elsaid et al., "Reduced Expression and Proteolytic Susceptibility of Lubricin/Superficial Zone Protein May Explain Early Elevation in the Coefficient of Friction in the Joints of Rats with Antigen-Induoed Arthritis," *Arthritis Rheum.* 56: 108-116, 2007.

EMBL Sequence Database Accession No. 092954, 1997.

EMBL Sequence Database Accession No. U70136, 1996.

Englert et al., "Inhibition of Integrative Cartilage Repair by Synovial Fluid Components," *Trans. Orthop. Res.* 29: 189, 2003.

Flannery et al., "Articular Cartiiage Superficial Zone Protein (SZP) is Homologous to Megakaryocyte Stimulating Factor Precursor and is a Multifunctional Proteoglycan with Potentiai Growth-Promoting, Cytoprotective, and Lubricating Properties in Cartilage Metabolism," *Biochem. Biophys. Res. Commun.* 254(3):535-041, 1999.

Garg et al., "The Structure of the O-Glycosylically-Linked Oligosaccharide Chains of LPG-I, a Glycoprotein Present in Articular Lubricating Fraction of Bovine Synovial Fluid," *Carbohydr. Res.* 78(1):79-88, 1980.

Hashimoto et al., "Synthesis of the First Tricomponent Bisubstrate Analogue that Exhibits Potent Inhibition Against GIcNAc:β-1,4-Galactosyltransferase," *J. Org. Chem.* 62:1914-1915, 1997.

Higaki et al., "Role of Constituents in Synovial-Fluid and Surface-Layer of Articular Cartilage in Joint Lubrication 2. The Boundary Lubricating Ability of Protein," *Journal of Japanese Society of Tribologists* vol. 40 N7, pp. 598-604, 1995.

Ikegawa et al., "Isolation, Characterization and Mapping of the Mouse and Human PRG4 (Proteoglycan 4) Genes," *Cytogenet. Cel. Genet.* 90: 291-297, 2000.

Jay et al., "Comparison of the Boundary-Lubricating Ability of Bovine Synovial Fluid, Lubricin, and Healon," J. Biomed. Mater. Res. 40:414-418, 1998.

Jay et al., "Analysis of the Frictional Characteristics of CACP Knockout Mice Joints with the Modified Stanton Pendulum Technique," *Trans. Orthop. Res.* 28:136, 2003.

Jay et al., "Boundary Lubrication by Lubricin is Mediated by O-Linked β (1-3) Gal-GalNAc Oligosaccharides," *Glycoconl. J.* 18:807-815. 2001.

Jay et al., "Characterization of a Bovine Synovial Fluid Lubricating Factor. I. Chemical, Surface Activity and Lubricating Properties," *Connect. Tissue Res.* 28(1-2):71-98, 1992.

Jay et al., "Characterization of a Bovine Synovial Fluid Lubricating Factor. II. Comparison with Purified Ocular and Salivary Mucin." *Connect. Tissue Res.* 28(1-2):69-98, 1992.

Jay et al., "Characterization of a Bovine Synovial Fluid Lubricating Factor. III. The Interaction with Hyaluronic Acid," *Connect. Tissue Res.* 28(4):245-55, 1992.

Jay, "Current Thinking on Viscosupplementation in Osteoarthritis," *Med. Health R.I.* 87:213-215, 2004.

Jay et al., "The Effect of Phospholipase Digestion Upon the Boundary Lubricating Ability of Synovial Fluid," *J. Rheumatol.* 26:2454-2457, 1999.

Jay et al., "Homology of Lubricin and Superficial Factor Zone Protein (SZP): Products of Megakaryocyte Stimulating Factor (MSF) Gene Expression by Human Synovial Fibroblast and Articular Chondrocytes Localized to Chromosome 1q25," *J. Orthopaedic. Res.* 19:677-687, 2001.

Jay et al., "Lubricating Ability of Aspirated Synovial Fluid from Emergency Department Patients with Knee Joint Synovitis," *J. Rheumatol.* 31:557-564, 2004.

Jay et al., "Lubricin is a Product of Megakaryocyte Stimulating Factor Gene Expression by Human Synovial Fibroblasts," *J. Rheumatol*, 27:594-600, 2000.

Jay et al., "Joint Lubrication: A Physicochemical Study of a Purified Lubrication Factor from Bovine Synovial Fluid" Thesis, Degree of Doctor of Philosophy, *Basis Health Sciences* (*Cellular and Molecular Pathology*), State University of New York (1990).

Jay et al., "Silver Staining of Extensively Glycosylated Proteins on Sodium Dodecyl Sulfate-Polyacrylamide Gels: Enhancement by Carbohydrate-Binding Dyes," *Anal. Biochem.* 185(2):324-330, 1990.

Kajihara et al., "Characterization of Inhibitory Activities and Binding Mode of Synthetic 6'-Modified Methyl N-Acetyl-β-Lactosaminide Toward Rat Liver CMP-D-Neu5Ac: D-Galactoside-2->6)-Alpha-D-Sialyltransferase," *Carbohyd. Res.* 247:179-193, 1993.

Khan et al., "A Trisaccharide Acceptor Analog for N-Acetylglucosaminyltransferase V Which Binds to the Enzyme but Sterically Precludes the Transfer Reaction," *J. Biol. Chem.* 268:2468-2473, 1993.

Kim et al., "A Rationally Designed Inhibitor of α-1,3-Galactosyltransferase," *J. Am. Chem. Soc.* 121:5829-5830, 1999.

(56) References Cited

OTHER PUBLICATIONS

Kuan et al., "Inhibition of Mucin Glycosylation by Aryl-N-Acetyl-α-Galactosaminides in Human Colon Cancer Cells," *J. Biol. Chem.* 264:19271-19277, 1989.

Lorenzo et al., "A Novel Catilage Protein (C1LP) Present in the Mid-zone of Human Articular Cartilage Increases with Age," *J. Biol. Chem.* 273:36 23469-23475, 1998.

Lorenzo et al.. "Cloning and Deduced Amino Acid Sequence of a Novel Cartilage Protein (C1LP) Identifies a Proform Including a Nucleotide Pyrophosphohydrolase," *J. Biol. Chem.* 273:23469-23475, 1998.

Lowary et al., "Recogniton of Synthetic O-Methyl, Epimeric, and Amino Analogues of the Acceptor α-L-Fuc p- (1-→2)-β-D-Gal p-OR by the Blood-Group A and B Gene-Specified Glycosyltransferases," *Carbohydr. Res.* 251:33-67, 1994.

Lu et al., "New Synthetic Trisaccharide Inhibitors for N-Acetylglucosaminyltransferase-V," *Bioorg. Med. Chem.* 4:2011-2022, 1996.

Merberg et al., "A Comparison of Vitronectin and Megakaryocyte Stimulating Factor," *Elsevier Science Publishers*, B.V., 45-53, 1993.

Miura et al., "Synthesis and Evaluation of Morpholino- and Pyrrolidinosphingolipids as Inhibitors of Glucosylceramide Synthase," *Bioorg. Med. Chem.* 6:1481-1489, 1996.

Muller et al., "Efficient Sialyltransferase Inhibitors Based on Transition-State Analogues of the Sialyl Donor." *Angewandte Chemie-Int Ed.* 37:2893-2897, 1998.

Murray et al., "Mechanism of Human α-1,3-Fucosyltransferase V: Glycosidic Cleavage Occurs Prior to Nucleophilic Attack," *Biochemistry* 36:823-831, 1997.

Neville et al., "Hydrophobic Glycosides of N-Acetylglucosamine Can Act as Primers for Polylactosamine Synthesis and Can Affect Glycollpid Synthesis in Vivo," *Biochem. J.* 307;791-707, 1995.

Obradovic et al., "Integration of Engineered Cartilage," *J. Orthop. Res.* 19:1089-1097. 2001.

Palcic et al., "A Bisubstrate Analog Inhibitor for α(1-→2)-Fucosyltransferase," *J. Biol. Chem.* 264:17174-17181, 1989.

Rhee et al., "The Secreted Glycoprotein Lubricin Protects Cartilage Surface and Inhibits Synovial Cell Overgrowth," *J. Clin. Invest.* 115:622-631, 2005.

Rogart et al., "Articular Collagen Degradation in the Hulth-Telhag Model of Osteoarthritis," *Osteoarthr. Cartil.* 7:539-547, 1999.

Sarkar et al., "Fucosylation of Disaccharide Precursors of Sialyl Lewis$^x$ Inhibit Selectin-Mediated Cell Adhesion," *J. Biol. Chem.* 272:25609-25616, 1997.

Schaefer et al, "Lubricin Reduces Carltiage—Cartilage Integration," *Biorheology* 41:503-508, 2004.

Schumacher et al., "Immunodetection and Partial cDNA Sequence of the Proteoglycan, Superficial Zone Protein, Synthesized by Cells Lining Synovial Joints," *J. Orthop. Res.* 17:110-121, 1999.

Schumacher et al., "A Novel Proteoglycan Synthesized and Secreted by Chondrocytes of the Superficial Zone of Articular Cartilage," *Arch. Biochem. Biophys.* 311:144-152, 1994.

Stults et al., "Characterization of the Substrate Specificity of α1,3-Galactosyltransferase Utiliziting Modified N-Acetyllactosamine Disaccharides," *Glycobiology* 9:681-668, 1999.

Sun et al., "Expression and Mapping of Lubricin in Canine Flexor Tendon," *J. Orthop. Res.* 24:1861-1863, 2006.

Sun et al., "Mapping Lubricin in Canine Musculoskeletal Tissues," *Connect. Tissue Res.* 47:215-221, 2006.

Swann et al., "The Molecular Structure and Lubricating Activity of Lubricin Isolated from Bovine and Human Synovial Fluids," *J. Biochem.* 225;195-201, 1985.

Swann et al., "The Molecular Structure of Lubricating Glycoprotein-I, the Boundry Lubricant for Articular Cartilage," *J. Biol. Chem.* 256(11):5921-2925. 1981.

Swann et al., "The Lubricating Activity of Human Synovial Fluids," *Arthritis Rheum.* 27:552-556, 1984.

Turner et al., "Purification, Biochemical Characterization, and Cloning of a Novel Megakaryocyte Stimulating Factor that has Megakaryocyte Colony Stimulating Activity," *Blood* 78 (Suppl. l):279, 1991.

Zappone et al. "Adsorption, Lubrication, and Wear of Lubricin on Model Surfaces: Polymer Brush-Like Behavior of a Glycoprotein," *Biophys. J.* 92:1693-1708, 2007.

SEQUENCE LISTING

```
<160> NUMBER OF SEQ ID NOS: 16

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
```

```
                290                 295                 300
Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
                340                 345                 350

Thr Thr Pro Lys Glu Pro Ala Ser Thr Thr Pro Lys Glu Pro Thr Pro
                355                 360                 365

Thr Thr Ile Lys Ser Ala Pro Thr Thr Pro Lys Glu Pro Ala Pro Thr
370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
                420                 425                 430

Lys Glu Pro Ala Pro Thr Thr Pro Lys Lys Pro Ala Pro Thr Thr Pro
                435                 440                 445

Lys Glu Pro Ala Pro Thr Thr Pro Lys Glu Pro Thr Pro Thr Thr Pro
450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Thr Lys Ser
                530                 535                 540

Ala Pro Thr Thr Pro Lys Glu Pro Ser Pro Thr Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
                580                 585                 590

Ala Pro Thr Thr Lys Lys Pro Ala Pro Thr Ala Pro Lys Glu Pro
                595                 600                 605

Ala Pro Thr Thr Pro Lys Glu Thr Ala Pro Thr Pro Lys Lys Leu
610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
                675                 680                 685

Ala Pro Thr Thr Pro Lys Glu Pro Ala Pro Thr Thr Pro Lys Glu Thr
                690                 695                 700

Ala Pro Thr Thr Pro Lys Gly Thr Ala Pro Thr Thr Leu Lys Glu Pro
705                 710                 715                 720
```

-continued

```
Ala Pro Thr Thr Pro Lys Lys Pro Ala Pro Lys Glu Leu Ala Pro Thr
                725                 730                 735

Thr Thr Lys Glu Pro Thr Ser Thr Thr Ser Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
        835                 840                 845

Thr Pro Pro Thr Thr Ser Glu Val Ser Thr Pro Thr Thr Thr Lys
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
        915                 920                 925

Glu Thr Thr Thr Ala Ala Pro Lys Met Thr Lys Glu Thr Ala Thr Thr
    930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
            980                 985                 990

Thr Thr Thr Glu Ile Met Asn Lys Pro Glu Glu Thr Ala Lys Pro Lys
        995                1000               1005

Asp Arg Ala Thr Asn Ser Lys Ala Thr Thr Pro Lys Pro Gln Lys
    1010                1015               1020

Pro Thr Lys Ala Pro Lys Lys Pro Thr Ser Thr Lys Lys Pro Lys
    1025                1030               1035

Thr Met Pro Arg Val Arg Lys Pro Lys Thr Thr Pro Thr Pro Arg
    1040                1045               1050

Lys Met Thr Ser Thr Met Pro Glu Leu Asn Pro Thr Ser Arg Ile
    1055                1060               1065

Ala Glu Ala Met Leu Gln Thr Thr Thr Arg Pro Asn Gln Thr Pro
    1070                1075               1080

Asn Ser Lys Leu Val Glu Val Asn Pro Lys Ser Glu Asp Ala Gly
    1085                1090               1095

Gly Ala Glu Gly Glu Thr Pro His Met Leu Leu Arg Pro His Val
    1100                1105               1110

Phe Met Pro Glu Val Thr Pro Asp Met Asp Tyr Leu Pro Arg Val
    1115                1120               1125

Pro Asn Gln Gly Ile Ile Ile Asn Pro Met Leu Ser Asp Glu Thr
    1130                1135               1140
```

```
Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Met Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac      60
ctgttgttgc tgctgtctgt tttcgtgatt cagcaagttt catctcaaga tttatcaagc     120
tgtgcaggga gatgtgggga agggtattct agagatgcca cctgcaactg tgattataac     180
tgtcaacact acatggagtg ctgccctgat ttcaagagag tctgcactgc ggagctttcc     240
tgtaaaggcc gctgctttga gtccttcgag agagggaggg agtgtgactg cgacgcccaa     300
tgtaagaagt atgacaagtg ctgtcccgat tatgagagtt tctgtgcaga agtgcataat     360
cccacatcac caccatcttc aaagaaagca cctccacctt caggagcatc tcaaaccatc     420
aaatcaacaa ccaaacgttc acccaaacca ccaacaagaa gaagactaa gaaagttata     480 gaatcagagg aaataacaga agaacattct gtttctgaaa atcaagagtc ctcctcctcc     540
```

```
tcctcctctt cctcttcttc ttcaacaatt tggaaaatca agtcttccaa aaattcagct    600
gctaatagag aattacagaa gaaactcaaa gtaaaagata caagaagaa cagaactaaa     660 aagaaaccta cccccaaacc accagttgta gatgaagctg gaagtggatt ggacaatggt    720
gacttcaagg tcacaactcc tgacacgtct accacccaac acaataaagt cagcacatct    780
cccaagatca aacagcaaa accaataaat cccagaccca gtcttccacc taattctgat     840
acatctaaag agacgtcttt gacagtgaat aaagagacaa cagttgaaac taaagaaact    900
actacaacaa ataaacagac ttcaactgat ggaaaagaga agactacttc cgctaaagag    960
acacaaagta tagagaaaac atctgctaaa gatttagcac ccacatctaa agtgctggct   1020
aaacctacac ccaaagctga aactacaacc aaaggccctg ctctcaccac tcccaaggag   1080
cccacgccca ccactcccaa ggagcctgca tctaccacac ccaaagagcc cacacctacc   1140
accatcaagt ctgcacccac cacccccaag gagcctgcac ccaccaccac caagtctgca   1200
cccaccactc ccaaggagcc tgcacccacc accaccaagg agcctgcacc caccactccc   1260
aaggagcctg cacccaccac caccaaggag cctgcaccca ccaccaa gtctgcaccc      1320 accactccca aggagcctgc acccaccacc ccaagaagc tgccccaac tacccccaag     1380 gagcctgcac ccaccactcc caaggagcct acacccacca ctcccaagga gcctgcaccc   1440
accaccaagg agcctgcacc caccactccc aaagagcctg cacccactgc ccccaagaag   1500
cctgccccaa ctaccccccaa ggagcctgca cccaccactc caaggagcc tgcacccacc   1560 accaccaagg agccttcacc caccactccc aaggagcctg cacccaccac caccaagtct   1620
gcacccacca ctaccaagga gcctgcaccc accactacca gtctgcacc caccactccc   1680 aaggagcctt cacccaccac caccaaggag cctgcaccca ccactcccaa ggagcctgca   1740
cccaccaccc ccaagaagcc tgccccaact accccccaagg agcctgcacc caccactccc   1800
aaggaacctg cacccaccac caccaagaag cctgcacccca ccgctcccaa agagcctgcc   1860
ccaactaccc ccaaggagac tgcacccacc accccccaaga agctcacgcc caccaccccc   1920
gagaagctcg cacccaccac ccctgagaag cccgcaccca ccacccctga ggagctcgca   1980
cccaccaccc ctgaggagcc cacacccacc accccctgagg agcctgctcc caccactccc   2040
aaggcagcgg ctcccaacac ccctaaggag cctgctccaa ctaccccctaa ggagcctgct   2100 ccaactaccc ctaaggagcc tgctccaact accccctaagg agactgctcc aactacccct   2160
aaagggactg ctccaactac cctcaaggaa cctgcaccca ctactcccaa gaagcctgcc   2220
cccaaggagc ttgcacccac caccaccaag gagcccacat ccaccacctc tgacaagccc   2280
gctccaacta cccctaaggg gactgctcca actaccccta aggagcctgc tccaactacc   2340
cctaaggagc ctgctccaac taccctaag gggactgctc caactaccct caaggaacct   2400
gcacccacta ctcccaagaa gcctgccccc aaggagcttg cacccaccac caccaagggg   2460
cccacatcca ccacctctga caagcctgct ccaactacac ctaaggagac tgctccaact   2520 accccccaagg agcctgcacc cactaccccc aagaagcctg ctccaactac tcctgagaca   2580
cctcctccaa ccacttcaga ggtctctact ccaactacca ccaaggagcc taccactatc   2640
cacaaaagcc ctgatgaatc aactcctgag ctttctgcag aacccacacc aaaagctctt   2700
gaaaacagtc ccaaggaacc tggtgtacct acaactaaga ctcctgcagc gactaaacct   2760
gaaatgacta caacagctaa agacaagaca acagaaagag acttacgtac tacacctgaa   2820
actacaactg ctgcacctaa gatgacaaaa gagacagcaa ctacaacaga aaaaactacc   2880
gaatccaaaa taacagctac aaccacacaa gtaacatcta ccacaactca agataccaca   2940
```

```
ccattcaaaa ttactactct taaaacaact actcttgcac ccaaagtaac tacaacaaaa    3000
aagacaatta ctaccactga gattatgaac aaacctgaag aaacagctaa accaaaagac    3060
agagctacta attctaaagc gacaactcct aaacctcaaa agccaaccaa agcacccaaa    3120
aaacccactt ctaccaaaaa gccaaaaaca atgcctagag tgagaaaacc aaagacgaca    3180
ccaactcccc gcaagatgac atcaacaatg ccagaattga accctacctc aagaatagca    3240
gaagccatgc tccaaaccac caccagacct aaccaaactc caaactccaa actagttgaa    3300
gtaaatccaa agagtgaaga tgcaggtggt gctgaaggag aaacacctca tatgcttctc    3360
aggccccatg tgttcatgcc tgaagttact cccgacatgg attacttacc gagagtaccc    3420
aatcaaggca ttatcatcaa tcccatgctt tccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaagatgc agggtacccc    3720
aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg aagaaggcc tgctctaaat    3900
tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
tttttctaaag atcaatacta taacattgat gtgcctagta aacagcaag agcaattact    4200
actcgttctg ggcagacctt atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc tttttgtgac acaagtacaa    4680
tctaaaagtt atattggaaa acatggaaat attaaaattt tacacttta ctagctaaaa    4740
cataatcaca aagctttatc gtgttgtata aaaaaattaa caatataatg gcaataggta    4800
gagatacaac aaatgaatat aacactataa cacttcatat tttccaaatc ttaatttgga    4860
tttaaggaag aaatcaataa atataaaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaa     5040
a                                                                    5041
```

<210> SEQ ID NO 3
<211> LENGTH: 7
<212> TYPE: PRT
<213> ORGANISM: Homo Sapiens

<400> SEQUENCE: 3

```
Lys Glu Pro Ala Pro Thr Thr
1               5
```

<210> SEQ ID NO 4
<211> LENGTH: 6
<212> TYPE: PRT
<213> ORGANISM: Homo Sapiens
<220> FEATURE:
<221> NAME/KEY: misc_feature
<222> LOCATION: (1)..(2)
<223> OTHER INFORMATION: Xaa = any amino acid
<220> FEATURE:
<221> NAME/KEY: misc_feature
<222> LOCATION: (6)..(6)
<223> OTHER INFORMATION: Xaa = any amino acid

<400> SEQUENCE: 4

```
Xaa Xaa Thr Thr Thr Xaa
1               5
```

<210> SEQ ID NO 5
<211> LENGTH: 6
<212> TYPE: PRT
<213> ORGANISM: Homo Sapiens

<400> SEQUENCE: 5

```
Glu Pro Ala Pro Thr Thr
1               5
```

<210> SEQ ID NO 6
<211> LENGTH: 6
<212> TYPE: PRT
<213> ORGANISM: Homo Sapiens

<400> SEQUENCE: 6

```
Pro Thr Thr Lys Glu Pro
1               5
```

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
agatttatca agctgtgcag ggag                                           24

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tttacaggaa agctccgcag tg                                             22

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
tcaaggtcac aactcctgac acg                                            23

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
ctctcggtaa gtaatccatg tcgg                                           24

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
ttgttgctgc tgtctgtttt cg                                             22

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
tggataaggt ctgcccagaa cgag                                           24

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct

<400> SEQUENCE: 13
tcaaggtcac aactcctgac acg                                            23

<210> SEQ ID NO 14
<211> LENGTH: 24
<212> TYPE: DNA
<213> ORGANISM: Artificial Sequence
<220> FEATURE:
<223> OTHER INFORMATION: Synthetic Construct

<400> SEQUENCE: 14
gatggtgtgt gtttgagaag gtcc                                           24

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
ccaaaccacc agttgtagat gaagc                                          25

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

```
<400> SEQUENCE: 16
gcggaagtag tcttctcttt tccatcag                                              28
```

TRIBONECTINS

This application is a continuation of U.S. application Ser. No. 12/703,036, filed on Feb. 9, 2010, and now abandoned, which is a divisional of U.S. application Ser. No. 12/608,462, filed on Oct. 29, 2009, issued as U.S. Pat. No. 8,026,346, which is a divisional of U.S. application Ser. No. 10/858,595, filed Jun. 1, 2004, issued as U.S. Pat. No. 7,618,941, which is a continuation of U.S. application Ser. No. 09/298,970, filed Apr. 23, 1999, issued as U.S. Pat. No. 6,743,774, the disclosures of each of which are incorporated by reference.

BACKGROUND OF THE INVENTION

The invention relates to lubrication of mammalian joints.

Osteoarthritis (OA) is the one of the most common form of joint disease. Factors which contribute to the development of OA include a family, history of OA, previous damage to the joint through injury or surgery, and age of the joint, i.e., "wear and tear" of the articulating surfaces of the joint. OA is very common in older age groups, but can affect children as well.

Current treatment is directed to relieving pain and other symptoms of OA, e.g., by administering analgesics and anti-inflammatory drugs. Other therapeutic approaches include viscosupplementation by administering hyaluronic acid and derivatives thereof to joint tissue to increase the viscosity of synovial fluid.

SUMMARY OF THE INVENTION

The invention features a novel treatment for osteoarthritis and other degenerative joint diseases by tribosupplementation. Tribosupplementation is carried out by administering lubricating polypeptides directly to the injured or arthritic joint. Unlike viscosupplementation, tribosupplementation does not substantially increase the viscosity of the solution, e.g, synovial fluid, to which it is added. The viscosity of a solution to which a tribonectin is added increases no more than 10%, preferably no more than 5%, more preferably no more than 2%, more preferably no more than 1%. Most preferably, the viscosity of the solution to which a tribonectin is added is unaltered or decreases.

Accordingly, the invention provides a tribonectin. A tribonectin is an artificial boundary lubricant which contains at least one repeat of an amino acid sequence which is at least 50% identical to KEPAPTT (SEQ ID NO:3). A tribonectin is formulated for administration to a mammalian joint. Preferably, the tribonectin is a recombinant or chemically-synthesized lubricating polypeptide. For example, a tribonectin includes a substantially pure polypeptide the amino acid sequence of which includes at least one but less than 76 subunits. Each subunit contains at least 7 amino acids (and typically, 10 or fewer amino acids). The amino acid sequence of each subunit is at least 50% identical to SEQ ID NO:3, and a non-identical amino acid in the reference sequence is a conservative amino acid substitution. For example, one or both of the threonine residues are substituted with a serine residue. Preferably, the amino acid sequence of the subunit is identical to SEQ ID NO:3. The tribonectin may also contain one or more repeats of the amino acid sequence XXTTX (SEQ ID NO:4). Polypeptides or other compounds described herein are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It can also be a 100 amino acid long polypeptide which is 50% identical to the reference polypeptide over its entire length.

A polypeptide or nucleic acid molecule which is "substantially identical" to a given reference polypeptide or nucleic acid molecule is a polypeptide or nucleic acid molecule having a sequence that has at least 85%, preferably 90%, and more preferably 95%, 98%, 99% or more identity to the sequence of the given reference polypeptide sequence or nucleic acid molecule. "Identity" has an art-recognized meaning and is calculated using well known published techniques, e.g., Computational Molecular Biology, 1988, Lesk A. M., ed., Oxford University Press, New York; Biocomputing: Informatics and Genome Projects, 1993, Smith, D. W., ed., Academic Press, New York; Computer Analysis of Sequence Data, Part I, 1994, Griffin, A. M. and Griffin, H. G., eds., Humana Press, New Jersey; Sequence Analysis in Molecular Biology, 1987, Heinje, G., Academic Press, New York; and Sequence Analysis Primer, 1991, Gribskov, M. and Devereux, J., eds., Stockton Press, New York). While there exist a number of methods to measure identity between two polynucleotide or polypeptide sequences, the term "identity" is well known to skilled artisans and has a definite meaning with respect to a given specified method. Sequence identity described herein is measured using the Sequence Analysis Software Package of the Genetics Computer Group (GCS), University of Wisconsin Biotechnology Center, 1710 University Avenue, Madison, Wis. 53705), with the default parameters as specified therein.

A tribonectin is characterized as reducing the coefficient of friction ($\mu$) between bearing surfaces. For example, reduction of friction is measured in vitro by detecting a reduction in friction in a friction apparatus using latex:glass bearings. Reduction of friction is also measured in viva, e.g., by measuring reduction of patient pain. Tribonectins of the invention are lubricating compositions. Polypeptides that have at least 50% (but less than 100%) amino acid sequence identity to a reference sequence are tested for lubricating function by measuring a reduction in the $\mu$ between bearing surfaces.

A tribonectin includes an O-linked oligosaccharide, e.g., an N-acetylgalactosamine and galactose in the form $\beta(1-3)$ Gal-GalNAC. For example, KEPAPTT (SEQ ID NO:3) and XXTTTX (SEQ ID NO:4) repeat domains are glycosylated by $\beta(1-3)$Gal-GalNAC (which may at times be capped with NeuAc in the form of $\beta(1-3)$Gal-GalNAC-NeuAc. The term "glycosylated" with respect to a polypeptide means that a carbohydrate moiety is present at one or more sites of the polypeptide molecule. For example, at least 10%, preferably at least 20%, more preferably at least 30%, and most preferably at least 40% of the tribonectin is glycosylated. Up to 50% or more of the tribonectin can be glycosylated. Per cent glycosylation is determined by weight.

A tribonectin polypeptide can contain a substantially pure fragment of megakaryocyte stimulating factor (MSF). For example, the molecular weight of a substantially pure tribonectin having an amino acid sequence of a naturally-occurring tribonectin is in the range of 220-280 kDa. Preferably, the apparent molecular weight of a tribonectin is less than 230 kDa, more preferably less than 250 kDa, and most preferably less than 280 kDa. A protein or polypeptide fragment is defined as a polypeptide which has an amino acid sequence that is identical to part, but not all, of the amino acid sequence of a naturally-occurring protein or polypeptide from which it is derived, e.g., MSF. The tribonectin may contain a polypeptide, the amino acid sequence of which is at least 50% identical to the sequence of residues 200-1140, inclusive, of SEQ ID NO:1, e.g., it contains the amino acid sequence of residues 200-1140, inclusive, of SEQ ID NO:1. In another example, the polypeptide contains an amino acid sequence that is at least 50% identical to the sequence of residues 200-1167, inclusive, of SEQ ID NO:1, e.g., one having the amino acid sequence identical to residues 200-1167, inclusive, of SEQ ID NO:1. The polypeptide contains an amino acid sequence that is at least 50% identical to the sequence of residues 200-1212, inclusive, of SEQ ID NO:1, e.g., the amino acid sequence of residues 200-1212, inclusive, of SEQ ID NO:1, or the polypeptide contains an amino acid sequence that is at least 50% identical to the sequence of residues 200-1263, inclusive, of SEQ ID NO:1, e.g., an amino acid sequence identical to residues 200-1263, inclusive, of SEQ ID NO:1. Preferably, the sequence of the polypeptide lacks the amino acid sequence of residues 1-24, inclusive, of SEQ ID NO:1 and/or the amino acid sequence of residues 67-104, inclusive of SEQ ID NO:1.

The invention also features an isolated nucleic acid molecule encoding a tribonectin. For example, the nucleic acid includes a sequence that is at least 50% identical to nucleotides 631-3453, inclusive, of SEQ ID NO:2. Preferably, the nucleic acid encodes a polypeptide with the amino acid sequence of residues 200-1140 of SEQ ID NO:1. For example, the nucleic acid has a nucleotide sequence identical to that of nucleotides 631-3453, inclusive, of SEQ ID NO:2, or a degenerate variant thereof. An isolated nucleic acid molecule is a nucleic acid molecule that is separated from the 5' and 3' coding sequences or non-coding sequences with which it is immediately contiguous in the naturally occurring genome of an organism. Isolated nucleic acid molecules include nucleic acid molecules which are not naturally occurring, e.g., nucleic acid molecules created by recombinant DNA techniques. For example, the nucleic acid of the invention includes nucleotides 631-3453, inclusive, of SEQ ID NO:2, but not nucleotides which are immediately contiguous to those sequences in the naturally-occurring genomic sequence or naturally-occurring cDNA.

Also within the invention is a method of lubricating a mammalian joint by contacting the joint with a tribonectin. The mammal is preferably a human, horse, dog, ox, donkey, mouse, rat, guinea pig, cow, sheep, pig, rabbit, monkey, or cat, and the joint is an articulating joint such as a knee, elbow, shoulder, hip, or any other weight-bearing joint. Tribonectins are administered intra-articularly. Therapeutic joint lubrication is also carried out by gene therapy, e.g., by contacting the joint or synovial fluid with a nucleic acid encoding a tribonectin. For example, nucleic acids are administered to a synovial cavity by intra-articular injection.

In addition to functioning as a boundary lubricant in a mammalian joint, a tribonectin is used as a boundary lubricant between soft mammalian tissues such as skin or internal organs or between a mammalian tissue and a medical-device such as a prosthetic implant. Accordingly, the invention encompasses a biocompatible composition containing a tribonectin in a form suitable for the inhibition of tissue adhesion formation. For example, the tribonectin is in the form of a film, membrane, foam, gel, or fiber. The term "film," as used herein, means a substance formed by compressing a foam or gel to a thin membrane, e.g., by casting into a flat mold and air drying to a thin membrane, or by compressing a gel or fibers, or by allowing or causing a gel or fibers to dehydrate. The term "foam," as used herein, means a substance with a porous structure formed, e.g., by introduction of as air into a tribonectin solution, suspension, gels, or fiber. The term "bioabsorbable," as used herein, refers to the ability of a tissue-compatible material to degrade in the body after implantation, into nontoxic products which are eliminated from the body or metabolized. A "biocompatible" substance, as the term is used herein, is one that has no medically unacceptable toxic or injurious effects on biological function. Tribonectin compositions for the prevention of adhesions are also formulated as compositions suitable for extrusion, e.g., to form a mold upon which tissue can grow without adhering.

A method inhibiting adhesion formation between a first surface and a second surface in a mammal is carried out by placing a tribonectin between the first and second surfaces in an amount sufficient to prevent adhesion of the surfaces in the mammal. For example, one or both of the surfaces is a mammalian tissue, and a tribonectin placed between them prevents formation of adhesions during the healing process. Alternatively the first or the second surface (or both) is an artificial device such as an orthopedic implant. Tissues to be treated include those injured by surgical incision or trauma.

Also within the invention is a method for diagnosing osteoarthritis or a predisposition thereto by obtaining a biological sample from a mammal and measuring the amount of an MSF fragment in the biological sample. An increase in the amount compared to a control, e.g, a predetermined value associated with a negative diagnosis or a biological sample from a mammal known to be free of osteoarthritis, indicates that the mammal suffers from osteoarthritis or is predisposed to developing osteoarthritis. Any biological sample is suitable for testing in the diagnostic method; typically, the biological sample is synovial fluid, blood, serum, or urine. Preferably, the MSF fragment contains the amino acid sequence of SEQ ID NO:3. Alternatively, the MSF fragment contains the amino acid sequence of EPAPTT (SEQ ID NO:5; a product of trypsin cleavage of a tribonectin) or the amino acid sequence of PTTKEP (SEQ ID NO:6; a product of elastase cleavage of a tribonectin).

Other features and advantages of the invention will be apparent from the following description of the preferred embodiments thereof, and from the claims.

DETAILED DESCRIPTION

A human lubricating polypeptide was purified from synovial fluid and found to contain amino acids encoded by exons 2 and 4-12 of the MSF gene (but not exons 1 or 3). The gene encoding naturally-occurring full length MSF contains 12 exons, and the naturally-occurring MSF gene product contains 1404 amino acids with multiple polypeptide sequence homologies to vitronectin including hemopexin-like and somatomedin-like regions. Centrally-located exon 6 contains 940 residues. Exon 6 encodes a O-glycosylated mucin domain. A polypeptide encoded by nucleotides 631-3453 of SEQ ID NO:2 provides boundary lubrication of articular cartilage.

TABLE 1

MSF amino acid sequence

MAWKTLPIYLLLLLSVFVIQQVSSQDLSSCAGRCGEGYSRDATCNCDYNCQHYMECCPDF
KRVCTAELSCKGRCFESFERGRECDCDAQCKKYDKCCPDYESFCAEVHNPTSPPSSKKAP
PPSGASQTIKSTTKRSPKPPNKKKTKKVIESEEITEEHSVSENQESSSSSSSSSSSSSTIW
KIKSSKNSAANRELQKKLKVKDNKKNRTKKKPTPKPPVVDEAGSGLANGDFKVTTPDTST
TQHNKVSTSPKITTAKPINPRPSLPPNSDTSKETSLTVNKETTVETKETTTTNKQTSTDG
KEKTTSAKETQSIEKTSAKDLAPTSKVLAKPTPKAETTTKGPALTTPKEPTFTTPKEPAS
TTPKEPTPTTIKSAPTTPKEPAPTTTKSAPTTPKEPAPTTTKEPAPTTPKEPAPTTTKEP
APTTTKSAPTTPKEPAPTTPKKPAPTTPKEPAPTTPKEPTPTTPKEPAPTTKEPAPTTPK
EPAPTAPKKPAPTTPKEPAPTTPKEPAPTTTKEPSPTTPKEPAPTTTKSAPTTTKEPAPT
TTKSAPTTPKEPSPTTTKEPAPTTPKEPAPTTPKKPAPTTPKEPAPTTPKEPAPTTTKKP
APTAPKEPAPTTPKETAPTTPKKLTPTTPEKLAPTTPEKPAPTTPEELAPTTPEEPTPTT
PEEPAPTTPKAAAPNTPKEPAPTTPKEPAPTTPKEPAPTTPKETAPTTPKGTAPTTLKEP
APTTPKKPAPKELAPTTTKEPTSTTSDKPAPTTPKGTAPTTPKEPAPTTPKEPAPTTPKG
TAPTTLKEPAPTTPKKPAPKELAPTTTKGPTSTTSDKPAPTTPKETAPTTPKEPAPTTPK
KPAPTTPETPPPTTSEVSTPTTTKEPTTIHKSPDESTPELSAEPTPKALENSPKEPGVPT
TKTPAATKPEMTTTAKDKTTERDLRTTPETTTAAPKMTKETATTTEKTTESKITATTTQV
TSTTTQDTTPFKITTLKTTTLAPKVTTTKKTITTTEIMNKPEETAKPKDRATNSKATTPK
PQKPTKAPKKPTSTKKPKTMPRVRKPKTTPTPRKMTSTMPELNPTSRIAEAMLQTTTRPN
QTPNSKLVEVNPKSEDAGGAEGETPHMLLRPHVFMPEVTPDMDYLPRVPNQGIIINPMLS
DETNICNGKPVDGLTTLRNGTLVAFRGHYFWMLSPFSPPSPARRITEVWGIPSPIDTVFT
RCNCEGKTFFFKDSQYWRFTNDIKDAGYPKPIFKGFGGLTGQIVAALSTAKYKNWPESVY
FFKRGGSIQQYIYKQEPVQKCPGRRPALNYPVYGEMTQVRRRRFERAIGPSQTHTTRIQY
SPARLAYQDKGVLHNEVKVSILWRGLPNVVTSAISLPNIRKPDGYDYYAFSKDQYYNIDV
PSRTARAITTRSGQTLSKVWYNCP (SEQ ID NO: 1)

TABLE 2

MSF TNA

```
   1 gcggccgcga ctattcggta cctgaaaaca acgatggcat ggaaaacact tcccatttac
  62 ctgttgttgc tgctgtctgt tttcgtgatt cagcaagttt catctcaaga tttatcaagc
 121 tgtgcaggga gatgtgggga agggtattct agagatgcca cctgcaactg tgattataac
 181 tgtcaacact acatggagtg ctgccctgat ttcaagagag tctgcactgc ggagctttcc
 241 tgtaaaggcc gctgctttga gtccttcgag agagggaggg agtgtgactg cgacgcccaa
 301 tgtaagaagt atgacaagtg ctgtcccgat tatgagagtt tctgtgcaga agtgcataat
 361 cccacatcac caccatcttc aaagaaagca cctccacctt caggagcatc tcaaaccatc
 421 aaatcaacaa ccaaacgttc acccaaacca ccaaacaaga agaagactaa gaaagttata
 481 gaatcagagg aaataacaga agaacattct gtttctgaaa atcaagagtc ctcctcctcc
 541 tcctcctctt cctcttcttc ttcaacaatt tggaaaatca agtcttccaa aaattcagct
```

EXON 6

```
 601 gctaatagag aattacagaa gaaactcaaa gtaaaagata caagaagaa cagaactaaa
 661 aagaaaccta cccccaaacc accagttgta gatgaagctg gaagtggatt ggacaatggt
 721 gacttcaagg tcacaactcc tgacacgtct accacccaac acaataaagt cagcacatct
 781 cccaagatca aacagcaaa accaataaat cccagaccca gtcttccacc taattctgat
 841 acatctaaag agacgtcttt gacagtgaat aaagagacaa cagttgaaac taaagaaact
 901 actacaacaa ataaacagac ttcaactgat ggaaaagaga agactacttc cgctaaagag
 961 acacaaagta tagagaaaac atctgctaaa gatttagcac ccacatctaa agtgctggct
1021 aaacctacac ccaaagctga aactacaacc aaaggccctg ctctcaccac tcccaaggag
1061 cccacgccca ccactcccaa ggagcctgca tctaccacac ccaaagagcc cacacctacc
1141 accatcaagt ctgcacccac caccccccaag gagcctgcac ccaccaccac caagtctgca
1201 cccaccactc ccaaggagcc tgcacccacc accaccaagg agcctgcacc caccactccc
1261 aaggagcctg cacccaccac caccaaggag cctgcaccca ccaccaccaa gtctgcaccc
1321 accactccca aggagcctgc acccaccacc cccaagaagc ctgccccaac taccccccaag
1181 gagcctgcac caccactccc caaggagcct acacccacca ctcccaagga gcctgcaccc
1441 accaccaagg agcctgcacc caccactccc aaagagcctg cacccactgc ccccaagaag
1501 cctgccccaa ctaccccaa ggagcctgca cccaccactc caaggagcc tgcacccacc
1561 accaccaagg agccttcacc caccactccc aaggagcctg cacccaccac caccaagtct
1621 gcacccacca ctaccaagga gcctgcaccc accactacca agtctgcacc caccactccc
1681 aaggagcctt cacccaccac caccaaggag cctgcaccca ccactcccaa ggagcctgca
1741 cccaccaccc caagaagcc tgcccaact accccaagg agcctgcacc caccactccc
1801 aaggaacctg cacccaccac caccaagaag cctgcaccca ccgctcccaa agagcctgcc
1861 caactaccc caaggagac tgcacccacc accccaaga agctcacgcc caccaccccc
1921 gagaagctcg cacccaccac ccctgagaag cccgcaccca ccaccctga ggagctcgca
1981 cccaccaccc ctgaggagcc cacacccacc accccctgagg agcctgctcc caccactccc
2041 aaggcagcgg ctcccaacac ccctaaggag cctgctccaa ctacccctaa ggagcctgct
2101 ccaactaccc ctaaggagcc tgctccaact accctaaagg agactgctcc aactaccccg
2161 aaagggactg ctccaactac cctcaaggaa cctgcacca ctactcccaa gaagcctgcc
2221 cccaaggagc ttgcacccac caccaccaag gagcccacat ccaccacctc tgacaagccc
```

TABLE 2 -continued

| MSF TNA |
|---|
| 2281 gctccaacta cccctaaggg gactgctcca actacccta aggagcctgc tccaactacc |
| 2341 cctaaggagc ctgctccaac taccccctaag gggactgctc aactaccct caaggaacct |
| 2401 ccacccacta ctcccaagaa gcctgccccc aaggagcttg cacccaccac caccaagggg |
| 2461 cccacatcca ccacctctga caagcctgct ccaactacac ctaaggagac tgctccaact |
| 2521 accccccaagg agcctgcacc cactaccccc aagaagcctg ctccaactac tcctgagaca |
| 2581 cctcctccaa ccacttcaga ggtctctact ccaactacca ccaaggagcc taccactatc |
| 2641 cacaaaagcc ctgatgaatc aactcctgag ctttctgcag aacccacacc aaaagctctt |
| 2701 gaaaacagtc ccaaggaacc tggtgtacct acaactaaga ctcctgcagc gactaaacct |
| 2761 gaaatgacta caacagctaa agacaagaca acagaaagag acttacgtac tacacctgaa |
| 2821 actacaactg ctgcacctaa gatgacaaaa gagacagcaa ctacaacaga aaaaactacc |
| 2881 gaatccaaaa taacagctac aaccacacaa gtaacatcta ccacaactca agataccaca |
| 2941 ccattcaaaa ttactactct taaaacaact actcttgcac ccaaagtaac tacaacaaaa |
| 3001 aagacaatta ctaccactga gattatgaac aaacctgaag aaacagctaa accaaaagac |
| 3061 agagctacta attctaaagc gacaactcct aaacctcaaa agccaaccaa agcacccaaa |
| 3121 aaacccactt ctaccaaaaa gccaaaaaca atgcctagag tgagaaaacc aaagacgaca |
| 3181 ccaactcccc gcaagatgac atcaacaatg ccagaattga ccctacctc aagaatagca |
| 3241 gaagccatgc tccaaaccac caccagacct aaccaaactc caaactccaa actagttgaa |
| 3301 gtaaatccaa agagtgaaga tgcaggtggt gctgaaggag aaacacctca tatgcttctc |
| 3361 aggccccatg tgttcatgcc tgaagttact cccgacatgg attacttacc gagagtaccc |
| 3421 aatcaaggca ttatcatcaa tcccatgctt tccgatgaga ccaatatatg caatggtaag |
| 3481 ccagtagatg gactgactac tttgcgcaat gggacattag ttgcattccg aggtcattat |
| 3541 ttctggatgc taagtccatt cagtccacca tctccagctc gcagaattac tgaagtttgg |
| 3601 ggtattcctt cccccattga tactgttttt actaggtgca actgtgaagg aaaaactttc |
| 3661 ttctttaagg attctcagta ctggcgtttt accaatgata taaaagatgc agggtacccc |
| 3721 aaaccaattt tcaaaggatt tggaggacta actggacaaa tagtggcagc gctttcaaca |
| 3781 gctaaatata agaactggcc tgaatctgtg tatttttcta agagaggtgg cagcattcag |
| 3841 cagtatattt ataaacagga acctgtacag aagtgccctg gaagaaggcc tgctctaaat |
| 3901 tatccagtgt atggagaaat gacacaggtt aggagacgtc gctttgaacg tgctatagga |
| 3961 ccttctcaaa cacacaccat cagaattcaa tattcacctg ccagactggc ttatcaagac |
| 4021 aaaggtgtcc ttcataatga agttaaagtg agtatactgt ggagaggact tccaaatgtg |
| 4081 gttacctcag ctatatcact gcccaacatc agaaaacctg acggctatga ttactatgcc |
| 4141 ttttctaaag atcaatacta taacattgat gtgcctagta aacagcaag agcaattact |
| 4201 actcgttctg gcagaccttt atccaaagtc tggtacaact gtccttagac tgatgagcaa |
| 4261 aggaggagtc aactaatgaa gaaatgaata ataaatttg acactgaaaa acatttatt |
| 4321 aataaagaat attgacatga gtataccagt ttatataaa aaatgttttt aaacttgaca |
| 4381 atcattacac taaaacagat ttgataatct tattcacagt tgttattgtt tacagaccat |
| 4441 ttaattaata tttcctctgt ttattcctcc tctccctccc attgcatggc tcacacctgt |
| 4501 aaaagaaaaa agaatcaaat tgaatatatc ttttaagaat tcaaaactag tgtattcact |
| 4561 taccctagtt cattataaaa aatatctagg cattgtggat ataaaactgt tgggtattct |

TABLE 2 -continued

MSF TNA

```
4621 acaacttcaa tggaaattat tacaagcaga ttaatccctc tttttgtgac acaagtacaa 4681 tctaaaagtt atattggaaa acatggaaat attaaaattt tacactttta ctagctaaaa 4741 cataatcaca aagctttatc gtgttgtata aaaaaattaa caatataatg gcaataggta 4801 gagatacaac aaatgaatat aacactataa cacttcatat tttccaaatc ttaatttgga 4861 tttaaggaag aaatcaacaa atataaaata taagcacata tttattatat atctaaggta 4921 tacaaatctg tctacatgaa gtttacagat tggtaaatat cacctgctca acatgtaatt 4961 atttaataaa actttggaac attaaaaaaa taaattggag gcttaaaaaa aaaaaaaaaa 5041 a (SEQ ID NO: 2)
```

TABLE 3

MSF Exon Boundaries

| Exon | Amino acid sequence in SEQ ID NO: 1 | Nucleotide sequence in SEQ ID NO: 2 |
|---|---|---|
| 1 | 1-24, inclusive | 34-105, inclusive |
| 2 | 25-66, inclusive | 106-231, inclusive |
| 3 | 67-104, inclusive | 232-345, inclusive |
| 4 | 105-155, inclusive | 346-498, inclusive |
| 5 | 156-199, inclusive | 499-630, inclusive |
| 6 | 200-1140, inclusive | 631-3453, inclusive |
| 7 | 1141-1167, inclusive | 3454-3534, inclusive |
| 8 | 1168-1212, inclusive | 3535-3670, inclusive |
| 9 | 1213-1263, inclusive | 3671-3822, inclusive |
| 10 | 1264-1331, inclusive | 3823-4026, inclusive |
| 11 | 1332-1371, inclusive | 4027-4146, inclusive |
| 12 | 1372-1404, inclusive | 4147-4245, inclusive |

TABLE 4

PCR Primers

| MSF exons | Forward Primer | Reverse Primer |
|---|---|---|
| exon 2 | 5'AGATTTATCAAGCTGT GCAGGGAG3' (SEQ ID NO: 7) | 5'TTTACAGGAAAGC TCCGCAGTG3' (SEQ ID NO: 8) |
| exon 6 | 5'TCAAGGTCACAACTCC TGACACG3' (SEQ ID NO: 9) | 5'CTCTCGGTAAGTA ATCCATGTCGG3' (SEQ ID NO: 10) |
| exons 2-12 | 5'TTGTTGCTGCTGTCTG TTTTCG3' (SEQ ID NO: 11) | 5'TGGATAAGGTCTG CCCAGAACGAG3' (SEQ ID NO: 12) |
| exons 6-12 | 5'TCAAGGTCACAACTCC TGACACG3' (SEQ ID NO: 13) | 5'GATGGTGTGTGTT TGAGAAGGTCC3' (SEQ ID NO: 14) |

The boundary lubricant isolated from synovial fluid is an alternatively-spliced variant of MSF. This alternatively-spliced variant was found to be the composition present in synovial fluid that confers lubricating capabilities to the articular joint. The boundary lubricant isolated from human synovial fluid contains amino acids encoded by exons 2, and 4-12 of the MSF gene, i.e., the alternative splice variant lacks amino acids encoded by exons 1 and 3 of the MSF gene. A recombinant or chemically-produced polypeptide containing at least exon 6 (but not exons 1 or 3) of MSF is useful to prevent and/or treat osteoarthritic disease. A recombinant or chemically-produced lubricating polypeptide containing at least one repeat of the amino acid sequence KEPAPTT (SEQ ID NO:3) either identically or with conservative substitution is also administered to lubricate mammalian joints.

Production and Purification of Recombinant Lubricating Polypeptides

To produce recombinant polypeptides, DNA containing exon 6 of MSF (nucleotides 631-3453 of SEQ ID NO:2) in an appropriate expression vector is transfected into a cell. The DNA can also contain some or all of exon 7 (nucleotides 354-3534 of SEQ ID NO:2), exon 8 (nucleotides 3535-3670 of SEQ ID NO:2), or exon 9 (nucleotides 3671-3822 of SEQ ID NO:2) of the MSF gene. Primers for polymerase chain reaction (PCR) methods to generate DNA which spans various exons of MSF are shown below.

Methods of designing forward and reverse primers used to make DNAs which encode tribonectin polypeptides of varying lengths and which incorporate various exons of the MSF gene, e.g., to make polypeptide encoded by exons 2, 4-12; exons 6-9; and exons 2, 4-9, are well known in the art of molecular, biology. Standard methods for transfecting cells with isolated nucleic acid are well known to those skilled in the art of molecular biology. For example, prokaryotic or eukaryotic cells in culture are transfected with the DNA of the invention operatively linked to expression control sequences appropriate for high-level expression in the cell. Such cells are useful for producing large amounts of the lubricating polypeptide, which are purified using standard methods. The lubricating polypeptides are used therapeutically for treatment or prevention of arthritic diseases. The polypeptides are also used to raise antibodies against a naturally-occurring or recombinantly-produced lubricating glycoproteins or glycopeptides.

For example, the recombinant gene product is expressed as a fusion protein and purified using a commercially available expression and purification system, e.g., the pFLAG expression system (IBI). The expression systems that may be used for purposes of the invention include, but are not limited to, microorganisms such as bacteria (e.g., E. coil and B. subtilis) transformed with recombinant bacteriophage DNA, plasmid DNA, or cosmid DNA expression vectors containing the nucleic acid molecules described herein. For production of glycosylated polypeptides, eukaryotic expression systems are used. Yeast (for example, Saccharomyces and Pichia) transformed with recombinant yeast expression vectors containing the recombinant nucleic acid encoding a tribonectin polypeptide are used. Insect cell systems infected with recombinant virus expression vectors (for example, baculovirus) containing the nucleic acid molecules encoding a tribonectin and mammalian cell systems (e.g., COS, CHO, BHK, 293, VERO, HeLa, MDCK, WI38, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter) are also useful. In addition to clinical applications, recombinant polypeptides are injected into a rabbit or rodent to produce antibodies as described below.

The synovial fluid of an inflamed or injured joint contains proteolytic enzymes that degrade lubricating proteins or polypeptides. For example, infiltrating immune cells such as neutrophils secrete trypsin and/or elastase. Even a minor injury to an articulating joint or an inflammatory state can result in cellular infiltration and proteolytic enzyme secretion resulting in traumatic synovitis. Synovitis for a period of a few days or weeks can result in the loss of the cytoprotective layer of a joint, which in turn leads to the loss of cartilage. Non-lubricated cartilaginous bearings may experience premature wear which may initiate osteoarthritis. Individuals who clinically present with a traumatic effusion (e.g., "water on the knee") are predisposed to developing osteoarthritis; the elaboration of proteolytic enzymes degrades and depletes naturally-occurring lubricating compositions in the synovial fluid. Depletion of natural lubricating compositions occurs in other inflammatory joint diseases such as rheumatoid arthritis. Replacing or supplementing the synovial fluid of such injured joints with the lubricating compositions of the invention prevents the development of osteoarthritis in the long term (e.g., years, even decades later) and immediately lubricates the joint to minimize short term damage.

Analogs, homologs, or mimetics of lubricating peptides which are less susceptible to degradation in vivo are used to lubricate mammalian joints. Analogs can differ from the naturally-occurring peptides by amino acid sequence, or by modifications which do not affect the sequence, or both. Modifications (which do not normally alter primary sequence); include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

Where proteolytic degradation of the peptides following injection into the subject is a problem, replacement of a particularly sensitive peptide bond with a noncleavable peptide mimetic bond renders the resulting peptide more stable, and thus more useful as a therapeutic. To render the therapeutic peptides less susceptible to cleavage by peptidases such as trypsin or elastase, the peptide bonds of a peptide may be replaced with an alternative type of covalent bond (a "peptide mimetic"). Trypsin, elastase, and other enzymes may be elaborated by infiltrating immune cells during joint inflammation. Trypsin cleaves a polypeptide bond on the carboxy-side of lysine and arginine; elastase cleaves on the carboxy-side of alanine, glycine. Thrombin, a serine protease which is present in hemorrhagic joints, cleaves a peptide bond on the carboxy-side of arginine. Collagenases are a family of enzymes produced by fibroblasts and chondrocytes when synovial metabolism is altered (e.g., during injury). These enzymes cut on the carboxy-side of glycine and proline. One or more peptidase-susceptible peptide bonds, e.g., those which appear in the KEPAPTT (SEQ ID NO:3) repeat sequence, are altered (e.g., replaced with a non-peptide bond) to make the site less susceptible to cleavage, thus increasing the clinical half-life of the therapeutic formulation.

Such mimetics, and methods of incorporating them into polypeptides, are well known in the art. Similarly, the replacement of an L-amino acid residue with a D-amino acid is a standard way of rendering the polypeptide less sensitive toproteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Clinical formulations of tribonectins may also contain peptidase inhibitors such as N-methoxysuccinyl-Ala-Ala-Pro-Val chloromethylketone (an inhibitor of elastase). Other clinically acceptable protease inhibitors (e.g., as described in Berling et al., 1998, Int. J. Pancreatology 24:9-17) such as leupeptin, aprotinin, α1-antitrypsin, α2-macroglobulin, α1-protease inhibitor, antichymotrypsin (ACHY), secretory leukocyte protease inhibitor (PSTI) are also co-administered with a tribonectin to reduce proteolytic cleavage and increase clinical half life. A cocktail of two or more protease inhibitors can also be coadministered.

Compositions of tribonectin polypeptides or nucleic acids encoding the polypeptides are formulated in standard physiologically-compatible excipients known in the art., e.g., phosphate-buffered saline (PBS). Other formulations and methods for making such formulations are well known and can be found in, e.g., "Remington's Pharmaceutical Sciences". Tribonectins are also formulated with non-crosslinked hyaluronic acid preparations or viscosupplementation compositions, such as cross-linked hyaluronic acid preparations. When a tribonectin is added to a viscosupplement formulation, the interaction of the tribonectin with hyaluronic acid reduces the viscosity of the viscosupplement.

Methods of making a glycopeptide and determining % glycosylation are known in the art, e.g., as described in U.S. Pat. No. 5,767,254. The presence of N-acetylgalactosamine is indicative of the presence of O-linked oligosaccharides (or Ser/Thr-linked oligosaccharides) in which GalNAc is commonly found in O-glycosidic alpha-linkage directly to amino acid. The presence of O-linked oligosaccharide is also detected by binding to Jacalin-Sepharose, an immobilized plant lectin that binds to the core disaccharide sequence Gal β (1-3)GalNAc linked to Ser/Thr in glycoproteins, or peanut agglutinin, which binds to β(1-3)Gal-GalNAC. O-linked oligosaccharides are distinguished from N-linked oligosaccharides using standard methods. For example, oligosaccharides in O-glycosidic linkage, but not in N-glycosidic linkage, are susceptible to release from peptide by treatment with mild base in the presence of sodium borohydride (50 mM NaOH, 1M NaBH$_4$, 16 hr at 45° C.) to cause a beta-elimination reaction.

Veterinary Applications

Canine osteoarthritis is a prevalent clinical disorder that is treated using the methods described herein. Osteoarthritis afflicts an estimated one in five adult dogs; an estimated 8 million dogs suffer from this degenerative, potentially debilitating disease. Yet, many owners do not recognize the signs of chronic canine pain. While any dog can develop osteoarthritis, those most at risk are large breeds, geriatric dogs, very active dogs (such as working or sporting animals), and those with inherited joint abnormalities such as hip or elbow dysplasia.

Equine degenerative joint disease such as osteoarthritis is a cause of lameness and impaired performance in horses. As with humans and other mammals, degenerative joint diseases which affect horses are progressive disorders of synovial joints characterized by articular cartilage degeneration and joint effusion. Acute or chronic trauma, overuse, developmental disease, joint instability and old age leads to synovitis, impaired chondrocyte metabolism, and the formation of fissures in the joint cartilage. Destructive enzymes such as trypsin, elastase, stromelysin and hyaluronidase are released into the joint where they degrade synovial fluid and cartilage components, resulting in decreased synovial fluid viscosity, poor lubrication, depressed cartilage metabolism and enhanced wear resulting in pain and cartilage erosion. Current therapeutic approaches include medications for pain relief and anti-inflammatory drugs. The compositions and methods described herein are useful to replenish the lubricating capabilities of the affected joint.

Administration of Therapeutic Polypeptides

Standard methods for delivery of peptides are used. Such methods are well known to those of ordinary skill in the art. For intra-articular administration, tribonectin is delivered to the synovial cavity at a concentration in the range of 20-500 μg/ml in a volume of approximately 0.1-2 ml per injection. For example, 1 ml of a tribonectin at a concentration of 250 μg/ml is injected into a knee joint using a fine (e.g., 14-22 gauge, preferably 18-22 gauge) needle. The compositions of the invention are also useful for parenteral administration, such as intravenous, subcutaneous, intramuscular, and intraperitoneal.

For prevention of surgical adhesions, the tribonectins described herein are administered in the form of gel, foam, fiber or fabric. A tribonectin formulated in such a manner is placed over and between damaged or exposed tissue interfaces in order to prevent adhesion formation between apposing surfaces. To be effective, the gel or film must remain in place and prevent tissue contact for a long enough time so that when the gel finally disperses and the tissues do come into contact, they will no longer have a tendency to adhere. Tribonectins formulated for inhibition or prevention of adhesion formation (e.g, in the form of a membrane, fabric, foam, or gel) are evaluated for prevention of post-surgical adhesions in a rat cecal abrasion model (Goldberg et al., In Gynecologic Surgery and Adhesion Prevention. Willey-Liss, pp. 191-204, 1993). Compositions, are placed around surgically abraded rat ceca, and compared to non-treated controls (animals whose ceca were abraded but did not receive any treatment). A reduction in the amount of adhesion formation in the rat model in the presence of the tribonectin formulation compared to the amount in the absence of the formulation indicates that the formulation is clinically effective to reduce tissue adhesion formation.

Tribonectins are also used to coat artificial limbs and joints prior to implantation into a mammal. For example, such devices are dipped or bathed in a solution of a tribonectin, e.g, as described in U.S. Pat. No. 5,709,020 or 5,702,456.

Lubricating polypeptides are at least about 10 amino acids (containing at least one KEPAPTT (SEQ ID NO:3)) or XXTTTX (SEQ ID NO:4) repeat), usually about 20 contiguous amino acids, preferably at least 40 contiguous amino acids, more preferably at least 50 contiguous amino acids, and most preferably at least about 60 to 80 contiguous amino acids in length. For example, the polypeptide is approximately 500 amino acids in length and contains 76 repeats of KEPAPTT (SEQ ID NO:3). The polypeptide is less than 1404 residues in length, e.g., it has the amino acid sequence of naturally-occurring MSF (SEQ ID NO:1) but lacks at least 5, 10, 15, 20, or 24 amino acids at the N-terminus of naturally-occurring MSF. Such peptides are generated by methods known to those skilled in the art, including proteolytic cleavage of a recombinant MSF protein, de novo synthesis, or genetic engineering, e.g., cloning and expression of at least exon 6, 7, 8, and/or 9 of the MSF gene.

Tribonectin polypeptides are also biochemically purified. The enzyme chymotrypsin cleaves at sites which bracket amino acids encoded by exon 6 of the MSF gene. Thus, a polypeptide containing amino acids encoded by exon 6 of the MSF gene (but not any other MSF exons) is prepared from a naturally-occurring or recombinantly produced MSF gene product by enzymatic digestion with chymotrypsin. The polypeptide is then subjected to standard biochemical purification methods to yield a substantially pure polypeptide suitable for therapeutic administration, evaluation of lubricating activity, or antibody production.

Therapeutic compositions are administered in a pharmaceutically acceptable carrier (e.g., physiological saline). Carriers are selected on the basis of mode and route of administration and standard pharmaceutical practice. A therapeutically effective amount of a therapeutic composition (e.g., lubricating polypeptide) is an amount which is capable of producing a medically desirable result, e.g., boundary lubrication of a mammalian joint, in a treated animal. A medically desirable result is a reduction in pain (measured, e.g., using a visual analog pain scale described in Peyron et al., 1993, J. Rheumatol. 20 (suppl.39):10-15) or increased ability to move the joint (measured, e.g., using pedometry as described in Belcher et al., 1997, J. Orthop. Trauma 11:106-109). Another method to measure lubricity of synovial fluid after treatment is to reaspirate a small volume of synovial fluid from the affected joint and test the lubricating properties in vitro using a friction apparatus as described herein.

As is well known in the medical arts, dosage for any one animal depends on many factors, including the animal's size, body surface area, age, the particular compound to be administered, sex, time and route of administration, general health, and other drugs being administered concurrently. Administration is generally local to an injured or inflamed joint. Alternatively, the polypeptides are administered via a timed-release implant placed in close proximity to a joint for slow release at the site of an injured or inflamed joint.

Gene Therapy

Gene therapy is carried out by administering to a mammal a nucleic acid encoding a therapeutic lubricating polypeptide, e.g., DNA encoding one or more repeats or the amino acid sequence KEPAPTT (SEQ ID NO:3) or DNA encoding a lubricating fragment of MSF, by standard vectors and/or gene delivery systems. Suitable gene delivery systems include liposomes, receptor-mediated delivery systems, naked DNA, and viral vectors such as herpes viruses, retroviruses, adenoviruses and adeno-associated viruses.

In addition to a gene delivery system as described above, the therapeutic composition may include a pharmaceutically acceptable carrier, e.g., a biologically compatible vehicle such as physiological saline, suitable for administration to an animal. A therapeutically effective amount of a nucleic acid or polypeptide composition is an amount which is capable of producing a medically desirable result in a treated animal, e.g., a reduction in pain associated with joint movement, an increase in lubricating function of synovial fluid.

Parenteral administration, such as intravenous, subcutaneous, intramuscular, and intraperitoneal delivery routes, may be used to deliver the compound. Preferably, therapeutic compositions such as nucleic acids or polypeptides are delivered intra-articularly. Dosage for any one patient depends upon many factors, including the patient's size, body surface area, age, the particular compound to be administered, sex, time and route of administration, general health, and other drugs (e.g., anti-inflammatory drugs, viscotherapeutic drugs) being administered concurrently. A preferred dosage for administration of nucleic acids is from approximately $10^6$ to $10^{22}$ copies of the nucleic acid molecule.

DNA is be introduced into target cells of the patient by standard vectors, e.g., a vector which contains DNA encoding a tribonectin operably linked to a promoter sequence. Suitable gene delivery systems may include liposomes, receptor-mediated delivery systems, naked DNA, and viral vectors such as herpes viruses, retroviruses, and adenoviruses, among others.

DNA may be administered locally using an adenovirus or adeno-associate virus delivery system using standard methods. For example, methods of delivering DNA intra-articularly to synovial fluid and methods of delivering DNA to cells from synovial fluid (e.g, synovial fibroblasts or chondrocytes) are described in U.S. Pat. No. 5,858,355. The only cis-acting sequences required for replication and packaging of recombinant adeno-associated virus own vector are the AAV terminal repeats. Up to 4 kb of DNA is inserted between the terminal repeats without effecting viral replication or packaging. To package a recombinant AAV vector, a plasmid containing the terminal repeats and DNA encoding a therapeutic polypeptide is co-transfected into cells with a plasmid that expresses. AAV rep and capsid proteins. The transfected cells are then infected with adeno-associated virus, and recombinant AAV virus containing the desired sequences is isolated from cells approximately 48-72 hours after transfection. Recombinant virus is then administered for gene therapy applications using known methods.

Electroporation is another method of introducing DNA into target cells, e.g., synovial fibroblasts or chondrocytes, ex vivo. Cells to be electroporated are placed into Hepes buffer saline (HBS) at a concentration of about $10^7$ cells per ml. The DNA to be electroporated is added at a concentration of approximately 5-20 µg/ml of HBS. The mixture is placed into an electroporation device and an electric field is applied according to standard protocols, e.g., in a range of between about 250 and 300 volts. Following introduction of DNA into synovial cells ex vivo, the genetically modified autologous synovial cells are transplanted back into the donor by intra-articular injection. Approximately $10^7$ cells are injected intra-articularly into joints in a volume of approximately 1 ml.

Synovial cells into which DNA is introduced are obtained using routine methods, e.g., through an arthroscope. The arthroscope is a small, hollow rod inserted into the knee via a small puncture wound which allows access to a surgical instrument to recover synovial cells arthroscopically. In some cases, the synovial cells in arthroscopically excised tissue are aseptically recovered by enzymatic digestion of the connective tissue matrix. For example, the synovium is cut into pieces of approximately 1 mm diameter and digested sequentially with trypsin (0.2% w/v in Gey's Balanced Salt Solution) for 30 minutes at 37° C., and collagenase (0.2% w/v in Gey's Balanced Salt Solution) for 2 hours at 37° C. A suspension of genetically-modified cells is injected into a recipient mammalian joint. Intra-articular injections of this type are routine and carried out in the doctor's office without additional surgical intervention. Repeat injections are carried out as needed.

Alternatively, the DNA (naked or packaged in a virus) is formulated in a suitable pharmaceutical carrier and injected intra-articularly. Gene therapy is also administered as a prophylactic measure to prevent the development of osteoarthritis in those individuals determined to be highly susceptible of developing this disease, e.g., those who have suffered an acute joint injury. Direct intra-articular injection of a DNA encoding a therapeutic polypeptide into a joint results in transfection of the recipient synovial cells to allow expression of DNA.

Drugs which stimulate an endogenous tribonectin promoter, e.g., TGFβ, may also be administered as described above to increase the level of synovial expression.

Production of Antibodies Specific for Synovial Lubricating Polypeptides

Antibodies specific for lubricating polypeptides are obtained by techniques well known in the art. Such antibodies can be polyclonal or monoclonal. Polyclonal antibodies can be obtained, for example, by the methods described in Ghose et al., Methods in Enzymology, Vol. 93, 326-327, 1983. For example, a lubricating polypeptide encoded by nucleotides 632-3453 of SEQ ID NO:2 is used as an immunogen to stimulate the production of polyclonal antibodies in the antisera of a rabbit. Similar methods can be used to raise antisera in animals such as goats, sheep, and rodents.

Monoclonal antibodies are obtained by the well known process described by Milstein and Kohler in Nature, 256:495-497, 1975, or as modified by Gerhard, Monoclonal Antibodies, Plenum Press, 1980, pages 370-371. Hybridomas are screened to identify those producing antibodies that are highly specific for a synovial lubricating polypeptide. Preferably, the antibody has an affinity of at least about $10^8$ liters/mole and more preferably, an affinity of at least about $10^9$ liters/mole. Monoclonal or polyclonal antibodies provide a means of rapidly purifying large quantities of recombinant lubricating polypeptides.

In addition to antibodies which are directed to the peptide core of a tribonectin, an antibody directed to a sugar portion or to a glycopeptide complex of a tribonectin is desirable. To generate an antibody to the peptide core, a peptide spanning amino acids 200-350 of SEQ ID NO:1 is used. Shorter peptides, e.g., 8-15 amino acids in length, which are identical to an 8-15 amino acid portion of amino acids 200-350 of SEQ ID NO:1 are also used to generate such antibodies. Other peptides to be used as immunogens for antibodies specific for the peptide core of a tribonectin include those which are in the region of amino acids 24-66 of SEQ ID NO:1, amino acids 105-155 of SEQ ID NO:1, or amino acids 156-199 of SEQ ID NO:1. To generate antibodies which bind to a glycosylated tribonectin polypeptide (but not a deglycosylated or nonglycosylated form), the immunogen is preferably a glycopeptide, the amino acid sequence of which spans a highly glycosylated portion of a tribonectin, e.g, a peptide with an amino acid sequence of residues 200-1140 of SEQ ID NO:1. Shorter glycopeptides, e.g., 8-15 amino acids in length, within the same highly glycosylated region are also used as immunogens. Methods of generating antibodies to highly glycosylated biomolecules are known in the art, e.g., as described by Schneerson et al., 1980, J. Exp. Med. 152:361-376.

Methods of Diagnosis

Osteoarthritis is a disease that develops slowly and is difficult to diagnose until its late stages when joint pain often compels an individual to seek medical treatment. Early diagnosis of osteoarthritis or a predisposition to develop the disease allows early intervention to prevent or reduce the development of advanced osteoarthritis. The invention provides methods of early detection of this disease or a predisposition to develop it by testing bodily fluids such as serum or urine for the presence of fragments of naturally-occurring tribonectins or the presence of fragments of MSF. Detection and quantitation of such peptides in biological fluids is well known in the art. For example, a standard sandwich ELISA assay is carried out using two different antibodies (e.g., a first antibody which binds to an oligosaccharide portion of the glycopeptide and a second antibody which binds to the peptide core of the glycopeptide) to a naturally-occurring tribonectin. Alternatively, standard protein sequencing by liquid chromatography and mass spectroscopy, as is described below, is used to detect MSF fragments in biological samples. A control value is a predetermined value associated with a negative diagnosis; alternatively, a control sample is a biological sample from a mammal known to be free of osteoarthritis. An increase in the amount compared to a control value or sample indicates that the mammal suffers from osteoarthritis or is predisposed to developing osteoarthritis.

Characterization of a Tribonectin from Human Synovial Fluid

Aliquots of synovial fluid from patients undergoing diagnostic arthroscopy and total knee replacement were collected and assayed in the friction apparatus. In both cases, the synovial fluid was aspirated prior to initiation of any surgical procedure and immediately centrifuged at 10,000×g at 4° C. for 2 hrs to remove cellular debris. Samples which were contaminated with blood were discarded. Aliquots with normal lubricating ability were pooled and stored at −20° C.

Purification and Isolation of a Tribonectin

Human synovial fluid (200 ml) was filtered through 0.22 µm sterile filter units (Nalgene) at 4° C. over two days. Retentate was scraped off filter membranes and resuspended with 50 mM NaAc buffer, pH 5.5, to the original synovial fluid volume containing proteolytic inhibitors: 1 mM phenylmethyl sulfonyl fluoride (PMSF), 1 mM parachloromercuricbenzoic acid (PCMB), and 10 mM ethylenediamine tetraacetate (EDTA). Digestion of hyaluronic acid was carried out at 37° C. by streptomyces hyaluronidase at 1 U/ml of resuspended synovial fluid. The digest was loaded on a DEAE column (Whatman International, Maidstone, UK) settled volume of 300 ml, equilibrated with NaAc buffer, 50 mM and washed with 1.5 L of the same buffer. The material with lubricating activity was eluted off of the DEAE matrix with 1 M NaCl. A 1 L wash was collected and concentrated via a 500 ml Amicon flow cell with an XM-100 membrane (mw cutoff 100 kDa). The concentrated sample was dialyzed against 25 mM phosphate buffer, pH 7.4, containing 0.15 M NaCl and 0.5 mM $CaCl_2$.

The DEAE-bound concentrate was loaded onto a peanut agglutinin (PNA)-agarose affinity column with a settled bed volume of 25 ml, equilibrated at room temperature with 25 mM phosphate and 0.15 NaCl buffer, pH 7.4. Unbound protein was eluted with the same buffer until absorbance at 230 and 280 nm decreased to background. Material with lubricating activity was maximally eluted in the presence of a stepwise gradient of α-lactose at a concentration of 0.07 M in 25 mM Tris and 0.15 M NaCl at pH 7.4. This material was loaded onto an Actigel ALD agarose (Sterogene Bioseparations, Arcadia, Calif.) coupled via amine groups to a murine monoclonal antibody against human fibronectin (Zymed Laboratories Inc., San Francisco, Calif.) to remove fibronectin as a contaminant. Eluted material was assayed for purity on SDS-PAGE (5-15% acrylamide) stained with Coomassie blue and by HPLC.

Protein electrophoresis standards were from GibcoBRL (Grand Island, N.Y.), and DNA ladder standard was from FMC Bioproducts (Rockland, Me.).

High Pressure Mould Chromatography

A µBondpak C18 3.9×150 mm column (Waters, Milford, Mass.) was eluted in reverse phase with 45% (v/v) methanol (Sigma) and 5% (v/v) acetonitrile (Aldrich) HPLC grade at 1 ml/min at 35° C. The eluate was assayed by a photo diode array detector PDA 996 (Waters), and material in peak fractions were analyzed by purity plots calculated using Millenium 32 software (Waters).

Friction Apparatus

A standard friction apparatus (e.g., an apparatus described by Jay et al., 1992, Conn. Tiss. Res. 28:71-88 or Jay et al., 1998, J. Biomed. Mater. Res. 40:414-418). Natural latex was oscillated against a ring of polished glass with a constant contact area of 1.59 $cm^2$. The bearing system was axially loaded within a gimbals system free to rotate around two perpendicular horizontal axes. Latex and glass as bearing materials were chosen because they offer a flat surface with small asperity heights on the order of 0.05 mm. Latex, like cartilage, is compliant. Within the gimbals system, these surfaces possess near perfect co-planarity. Accordingly, fluid wedges were not generated and only a thin layer of boundary fluid was present. The entraining velocity (i.e., sliding speed) was 0.37 mm/sec with a constant contact pressure of $0.35 \times 10^6$ $N/m^2$.

The friction apparatus recorded displacements of the gimbals system around the vertical loading axis through a linear displacement voltage transducer, the output voltage of which was directly proportional to the magnitude of the frictional torque. The peak to peak amplitude of this signal was related to µ by a previous calibration with known frictional torque.

Test surfaces were cleaned extensively before use. A 3.8× 3.8 cm piece of latex strapped onto the stainless steel stud was washed under running distilled deionized water (DDW) for 2 min. It was then placed in a shallow bath of 0.9% NaCl physiological saline (PS). The glass slide was scrubbed with a 1% (v/v) 7× detergent (Flow Laboratories, McLean, Va.) solution in DDW for 10 min and then allowed to soak in the same solution at 100° C. A 5 min. scrubbing was also performed with the hot 7× solution followed by rinsing for 2-4 min. under running DDW.

The µ was measured at 35° C. and was preceded by a baseline measurement of the µ with PS. Lubrication was manifested by a reduction of µ relative to the µ of PS. Negative delta µ values indicate lubrication, whereas positive values indicate friction. Addition of 200 µl of PS and later 200 µl of test lubricant was followed by bringing the bearing surfaces close enough so that the solution wet both surfaces. After 5 min for equilibration, the latex-coated bearing was brought to rest on the glass as it was oscillating. Peak to peak voltages were automatically recorded after 1, 3 and 5 mins. At this point, the surfaces were separated for 2 min. and then brought back together for another 5 min session. The 3 and 5 min. µ values of the last two 5 min. sessions typically stabilized and were recorded.

Human serum fibronectin was purchased from Sigma Chemical (F0895, St. Louis, Mo.) and dialyzed against PS before use in the friction apparatus.

Boundary lubricants exert their effect by changing the physico-chemical characteristics of a surface. Bearing surfaces must generate a mutual repulsion in order to be lubricated in the boundary mode. Typical room temperature examples of boundary lubricants are graphite, teflon and molybdenum sulphide. Such compositions reduce friction between bearing surfaces, and therefore, are used as positive controls in assay to measure the lubricating properties of tribonectins. Tribonectins are boundary lubricants that can have an amphipathic character by coating non-biologic hydrophobic surfaces such as latex. The oligosaccharide component of a tribonectin networks with the surrounding aqueous environment. When the ultimate and penultimate sugars are removed from a naturally-occurring tribonectin purified from synovial fluid, the lubricating ability is eliminated.

The latex:glass arthrotripsometer offers an expedient way to test purified biological lubricating factors repetitively with reproducibility. Natural latex and polished glass represent bearing surfaces with little if any variation in physico-chemical characteristic from test to test. By contrast, resected cartilage apposed to either polished glass or cartilage itself will experience deformation that cannot be accurately controlled. The μ observed in a cartilage-cartilage bearing lubricated by synovial fluid was between 0.005 and 0.024. The values of μ in the latex:glass system were appreciably higher and typically 0.04 or less. Differences in μ between the bearing materials are attributed to the 80% (w/w) water content of cartilage.

Protein Sequencing by Liquid Chromatography and Mass Spectrometry (LCMS)

Standard LCMS was carried out on tryptic digests of the purified lubricating material described above. Excised bands from 2 mm thick 5-20% gradient SDS-PAGE gels (Bio-rad Laboratories, Hercules, Calif.) containing the lubricating material was analyzed. The material was deglycosylated by NaNase III and O-glycosidase DS (Glyko, Novato, Calif.). Deglycosylation was carried out with the above enzymes at activities of 0.17 U/ml and 0.10 U/ml, respectively, for 18 hrs in the presence of 0.5 mg/ml of a tribonectin purified from synovial fluid. In all cases, the gel slices were cut through the middle of the band and were 16 mm$^3$ in size. All contact surfaces were carefully cleaned with 50% (v/v) acetonitrile. Sequence data was entered into the BLAST GENBANX® search algorithm and matches identified.

Isolation and Culture of Human Synovial Fibroblasts

Human synovium with a normal appearance was obtained from a 30 year old white male undergoing arthroscopy. Within 1 hr after surgery, the synovial tissue explant was washed three times with Dulbecco's calcium- and magnesium-free phosphate-buffered saline (GIBCO). Pieces 2 mm$^3$ in size were placed in Dulbecco's modification of Eagle's medium (GIBCO), supplemented with 100 U of penicillin and 100 μg of streptomycin per ml (GIBCO), containing 4 mg/ml of Clostridiopeptidase A (Worthington Biochemical CLS, 125-200 U/mg) sterilized through a 0.22 μm filter (Nalge). The tissue fragments were further divided with scissors in a 100 mm plastic petri dish (Falcon) and incubated for 4 hrs in 20 ml of medium at 37° C. in a moist atmosphere of 5% carbon dioxide and 95% air.

The digest was well mixed many times by aspiration into and expulsion from a Pasteur pipette. An equal volume of 0.05% trypsin and 0.02% EDTA in modified Puck's Saline A (GISCO) were added and incubation continued for a further hour under the same conditions. The suspension was centrifuged 10 min at 400×g at 23° C. and washed three times each with 40 ml of calcium- and magnesium-free phosphate-buffered saline. The pellet was suspended in modified Eagle's medium (20 ml) supplemented with 10% fetal bovine serum (Flow Laboratories), 100 U of penicillin, and 100 mg of streptomycin per ml. Two milliliters of this final mixture were plated per 60 mm plastic petri dish (Falcon). Synovial fibroblasts were grown to confluence and cells harvested. Human skin fibroblasts (American Type Culture Collection (ATCC) Designation CCD-1099SK; ATCC, Mannassas, Va.) which served as a control were also grown and harvested using the above procedure.

RNA Extraction and RT-PCR Analyses

RNA from synovial and skin fibroblasts was purified by RNeasy mini-columns and reagents (Qiagen, Crawley, Ltd., UK). Contaminating genomic DNA was removed by DNAshredder and DNase (RNase free) (Qiagen). First strand cDNA was synthesized by reverse transcription and PCR amplification using the following oligonucleotide primers. MSF-exon 6 forward primer 5'-CCAAACCACCAGTTGTA-GATGAAGC-3' (SEQ ID NO:15) and MSF-exon 6 reverse primer 5'-GCGGAAGTAGTCTTCTCTTTTCCATCAG-3' (SEQ ID NO:16). These primers correspond to nucleotide position numbers 674-698 and 953-926, respectively, of the human MSF gene (SEQ ID NO:2; GENBANK® accession number U70136). Thermal cycling conditions were 42° C. for 12 mins., 95° C. for 10 mins., followed by 43 cycles between 94° C.×20 secs and 55-65° C.×30-90 secs. A final extension for 7 mins was at 72° C. (Perkin Elmer Biosystems).

Alternative Splice Variant of MSF is a Tribonectin

A lubricating polypeptide was purified from human synovial fluid using standard biochemical methods followed by affinity chromatography with peanut agglutinin. The final fraction, which solely possessed lubricating ability, contained a product with an apparent molecular weight of 280 kDa. Components with a molecular weight in excess of 280 kDa were not observed. LCMS performed on tryptic fragments from the 280 kDa excised band indicated the presence of two different proteins that matched in the BLAST search algorithm to fibronectin precursor and MSF (GenBank Accession No. U70136). Sequences of MSF were identified from both native and deglycosylated lubricating polypeptides. Accordingly, the purification scheme was terminated with an anti-fibronectin column resulting in the elimination of fibronectin as an impurity (as assayed by C18 analytical HPLC and purity plot analysis). In addition, lower molecular weight bands at 70 and 160 kDa on SDS-PAGE were absent from the purified tribonectin preparation eluting from the anti-fibronectin column. The purified tribonectin assayed in the friction apparatus was found to display boundary lubricating activity similar to that of whole synovial fluid (Table 5). By contrast, purified serum fibronectin raised friction indicating that synovial fluid lubricating ability was mediated by the purified tribonectin.

TABLE 5

Friction coefficients for a tribonectin purified from human synovial fluid and fibronectin (Mean +SD; N = 3)

| LUBRICANT* | μ | μ (PS**) | Δμ |
| --- | --- | --- | --- |
| Tribonectin | 0.047 ± .006 | 0.131 ± .007 | −0.084 ± .004 |
| HSF† | 0.040 ± .005 | 0.135 ± .009 | −0.095 ± .011 |
| Fibronectin | 0.181 | 0.136 | +0.045 ± .005 |

Tested at a concentration of 250 μg/ml in PS.
Physiological saline.
Post-Mortem Human Synovial Fluid Furthermore, LCMS of tryptic fragments identified portions of exons 6 through 9 of MSF, inclusively. Purified tribonectin reacted to peanut agglutinin indicating the presence of β(1-3)Gal-GalNAC oligosaccharides by virtue of its purification. An increase in electrophoretic mobility was observed after digestion with NaNase III and O-glycosidase DS, indicating that the purified tribonectin is highly glycosylated via O-linked oligosaccharides. The apparent molecular weight of deglycosylated tribonectin purified from synovial fluid was 120 kDa.

RT-PCR analysis was completed using primers specific for nucleotide sequences encoding the N-terminal end of exon 6 of MSF. RT-PCR's using human synovial fibroblast RNA generated a 280 bp product, the predicted distance between the designed primers. Similar experiments without reverse transcriptase did not generate this product indicating that the RNA was free of genomic DNA. Purified RNA from skin fibroblasts did not produce any product using the same primers.

MSF was first isolated from human monocytes; a 25 kDa fragment of MSF was found to stimulate the development of megakaryocytes. MSF precursor protein is 1404 residues in size and constructed from 12 exons. Exon 6 appears to encodes a centrally located mucin that is 940 residues in length. Exon 6 has homology to vitronectin, exons 2 and 3 appear homologous to somatomedin B-like regions, and exons 8, 9 are similar to hemopexin-like regions in vitronectin. Hemopexin is a serum hems scavenging protein that interacts with hyaluronate.

A tribonectin purified from synovial fluid and an articular cartilage superficial zone protein (SZP) purified from articular cartilage share sequence identity with MSF but differ in their apparent molecular weights and amino acid sequences.

Other embodiments are within the following claims.

What is claimed is:

1. A method of reducing the coefficient of friction between tissue surfaces comprising administering a composition in an amount sufficient to lubricate a tissue surface, the composition comprising a tribonectin polypeptide comprising a lubricating polypeptide or a biologically active fragment thereof and an O-linked β(1-3) Gal-GalNAc oligosaccharide, the lubricating polypeptide or fragment comprising residues 200-1140 of sequence ID NO: 1 or a peptide mimetic thereof.

2. The method of claim 1, wherein said tribonectin polypeptide comprises repeats of an amino acid sequence of sequence ID NO: 3.

3. The method of claim 2, wherein said tribonectin polypeptide comprises fewer than 76 of said repeats.

4. The method of claim 1, wherein said tribonectin polypeptide reduces the coefficient of friction between surfaces in vitro.

5. The method of claim 1, wherein said tribonectin polypeptide reduces the coefficient of friction between bearing articular cartilage surfaces in vivo.

6. The method of claim 1, wherein the molecular weight of said tribonectin polypeptide is in the range of 220-280 kDa.

7. The method of claim 1, wherein said tribonectin polypeptide comprises a fragment of megakaryocyte stimulating factor.

8. The method of claim 1, wherein said tribonectin polypeptide comprises an amino acid sequence that comprises a multiplicity of subunits comprising at least one glycosylated threonine.

9. The method of claim 1, wherein said tribonectin polypeptide lacks the amino acid sequence of residues 1-24, inclusive, of SEQ ID NO: 1, or residues 67-104, inclusive, of SEQ ID NO: 1.

10. The method of claim 1, further comprising administering to a bearing surface hyaluronic acid.

11. The method of claim 1, wherein said tissue surfaces comprise bearing surfaces.

12. The method of claim 1, comprising administering said composition to a human in a form suitable for the inhibition of tissue adhesion formation.

13. The method of claim 1, comprising administering said composition to a human in an amount sufficient to lubricate bearing human tissue surfaces.

14. The method of claim 13, comprising placing said composition between first and second human tissue surfaces having reduced lubrication.

15. The method of claim 1, wherein said polypeptide lubricates an articulating joint of a human, dog, or horse.

16. The method of claim 1, wherein said composition is in the form of a film, membrane, foam, gel or fiber.

17. The method of claim 1, wherein said composition comprises a 20 to 500 μg/mL of said polypeptide.

18. The method of claim 17, wherein said composition comprises 250 μg/mL of said polypeptide.

19. The method of claim 1, wherein said composition is administered by injection.

20. A method of reducing the coefficient of friction between a tissue surface and an artificial device, comprising administering a composition in an amount sufficient to lubricate the tissue surface in contact with the artificial device, the composition comprising a tribonectin polypeptide comprising a lubricating polypeptide or a biologically active fragment thereof and an O-linked β(1-3) Gal-GalNAc oligosaccharide, the lubricating polypeptide or fragment comprising residues 200-1140 of sequence ID NO: 1 or a peptide mimetic thereof.

* * * * *